United States Patent [19]

Paget, Jr. et al.

[11] Patent Number: 4,835,168

[45] Date of Patent: May 30, 1989

[54] THIADIAZOLE ANTIVIRAL AGENTS

[75] Inventors: Charles J. Paget, Jr., Indianapolis; Brent J. Rieder, Greenfield; Wayne A. Spitzer; Chyun-Yeh E. Wu, both of Indianapolis, all of Ind.

[73] Assignee: Eli Lilly and Company, Indianapolis, Ind.

[21] Appl. No.: 165,967

[22] Filed: Mar. 9, 1988

Related U.S. Application Data

[63] Continuation-in-part of Ser. No. 932,425, Nov. 19, 1986, abandoned, which is a continuation-in-part of Ser. No. 809,669, Dec. 16, 1985, abandoned.

[51] Int. Cl.$^4$ .................... C07D 285/12; A61K 31/41
[52] U.S. Cl. .................... 514/363; 514/342; 546/277; 548/138
[58] Field of Search ............. 548/138; 514/363, 342; 546/277

[56] References Cited

U.S. PATENT DOCUMENTS 3,891,762  6/1975  Wakae et al. .................. 424/270

FOREIGN PATENT DOCUMENTS

| 229501 | 7/1987 | European Pat. Off. . |
| 23517 | 7/1987 | Iran . |
| 46-35262 | 10/1971 | Japan . |
| 4720344 | 9/1972 | Japan .................. 548/138 |
| 4747388 | 11/1972 | Japan .................. 548/138 |
| 48-466 | 1/1973 | Japan . |
| 49-07218 | 2/1974 | Japan . |

OTHER PUBLICATIONS

Naik et al., *J. Indian Chem. Soc.*, vol. LX, Jul. 1983, pp. 674–678.
Grant et al., *J. Med. Chem.*, vol. 15, No. 10, 1972, pp. 1082–1084.
Russo et al., *Farmaco*, Ed. Sci. 1975, 30(12) 1031–1038.
Malineski et al., *Virology*, 110, 281–291 (1981).
Nelson et al., *Cancer Res.* 37, 182–187 (1977).
Bonina et al., Antimicrobial Agents and Chemotherapy, Dec. 1982, 1067–1069.
Widell et al., *Antiviral Research*, 6 103–112 (1986).
Murakami et al., *Synthesis*, 9 738–740 (1984).

*Primary Examiner*—Robert Gerstl
*Attorney, Agent, or Firm*—Douglas J. Taylor; Leroy Whitaker

[57] ABSTRACT

Compounds of formula (I)

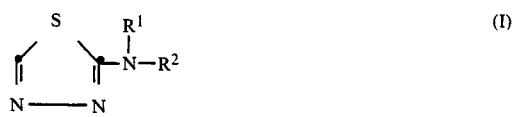

wherein $R^1$ is hydrogen, and $R^2$ is cyano or —C(=S)—NH—$R^3$; or $R^1$ and $R^2$ taken together are =C(NH$_2$)$_2$ or =C($R^5$)(NH$R^{3'}$);

$R^3$ and $R^{3'}$ are hydrogen or —COO$R^4$;

$R^4$ is $C_1$-$C_{10}$ alkyl, substituted $C_1$-$C_{10}$ alkyl, $C_2$-$C_{10}$ alkenyl, substituted $C_2$-$C_{10}$ alkenyl, phenyl, or substituted phenyl; and $R^5$ is hydrogen or —S—$R^6$ where $R^6$ is $C_1$-$C_4$ alkyl, cyano-$C_1$-$C_4$ alkyl or pyridyl-$C_1$-$C_4$ alkyl, and salts thereof, are useful antiviral agents.

21 Claims, No Drawings

THIADIAZOLE ANTIVIRAL AGENTS

CROSS-REFERENCE

This is a continuation-in-part of U.S. Ser. No. 06/932,425, filed Nov. 19, 1986, now abandoned, which is a continuation-in-part of U.S. Ser. No. 809,669, filed Dec. 16, 1985, now abandoned.

BACKGROUND OF THE INVENTION

Diseases caused by one or more viruses are becoming alarmingly prevalent. Sexually transmitted viral infections and those transmitted by blood transfusion have been the focus of intensive research efforts over the past several years. Less severe diseases caused by viruses include the common cold.

Few truly effective antiviral agents have been developed, and in many cases the only treatment available is antibacterial agents, not to combat the virus but rather to ward off invasion of a weakened biological system by bacteria. The search continues for effective antiviral agents to treat and control common ailments such as influenza and colds, diseases caused by the various strains of herpes virus as well as to combat more severe viral infections such as acquired immune deficiency syndrome (AIDS).

This invention concerns the discovery that certain 2-amino-1,3,4-thiadiazole derivatives are useful in treating certain types of viral infections. Thiadiazoles are in general well known in the art. Some have been employed in the medical field. For example, Naik et al. describe the antimicrobial activities of a number of thiadiazolylthiazolidinones; *J. Indian Chem. Soc.*, Vol. LX, July 1983, pp 674–678. Grant et al., in *J. Med. Chem.*, Vol. 15, No. 10, 1972, pp 1082–1084, disclose that certain amine substituted derivatives of 2-amino-1,3,4-thiadiazole are useful hypotensive agents. U.S. Pat. No. 3,772,316 describes a class of N-acylated 2-amino-1,3,4-thiadiazoles which are said to be useful as fungicides. Russo et al., in *Farmaco. Ed. Sci.*, Vol. 30, No. 12, 1975, pp 1031–1038, describe a series of thiourea derivatives of 1,3,4-thiadiazole and their cyclization products. The compounds are said to be antibacterial agents. Malinoski et al., in *Virology*, 110, 281–291 (1981) describes certain antiviral activity of 2-amino-1,3,4-thiadiazole.

In one embodiment, this invention provides a method for preventing, treating and controlling certain types of viral infections. More particularly one embodiment provides an in vitro antiviral method for protecting mammalian cells in culture which comprises adding to the culture an antiviral amount of a compound of formula (I):

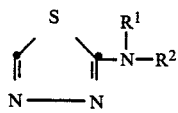
(I)

wherein:
$R^1$ is hydrogen, and $R^2$ is cyano or $-C(=S)-NH-R^3$; or
$R^1$ and $R^2$ taken together are $=C(NH_2)_2$ or $=C(R^5)(NHR^{3'})$;
$R^3$ and $R^{3'}$ are hydrogen or $-COOR^4$;

$R^4$ is $C_1-C_{10}$ alkyl, substituted $C_1-C_{10}$ alkyl, $C_2-C_{10}$ alkenyl, substituted $C_2-C_{10}$ alkenyl, phenyl, or substituted phenyl; and
$R^5$ is hydrogen or $-S-R^6$ where $R^6$ is $C_1-C_4$ alkyl, cyano-$C_1-C_4$ alkyl or pyridyl-$C_1-C_4$ alkyl.

The compounds of formula (I) are also useful in treatment of animals suffering from a viral infection or susceptible thereto. For this purpose, prefered compounds are those of the formulas (II), (III) and (IV):

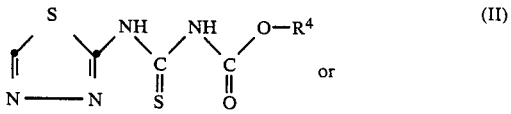
(II)

or

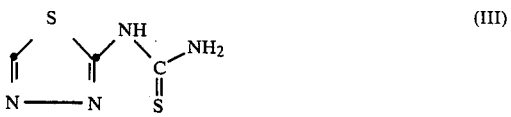
(III)

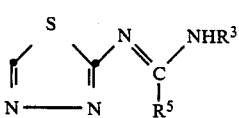
(IV)

where $R^3$ is hydrogen or $-COOR^4$, $R^5$ is hydrogen or $-S-R^6$, and $R^6$ is $C_1-C_4$ alkyl.

The invention also provides a series of preferred new compounds defined by the formulas (V), (VI), and (VII):

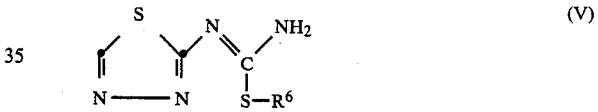
(V)

(VI)

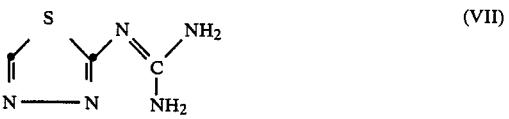
(VII)

The compound of formula (V) is particularly useful as an in vivo antiviral. The compound of formula (VI) possesses both in vitro and in vivo antiviral activity, while the compound of formula (VII) is extremely active in vitro. The invention additionally embraces the use of pharmaceutically acceptable salts of the foregoing compounds.

Several of the thiadiazoles employed in the antiviral method of this invention are known in the art. All of the compounds can be prepared by chemical processes available, for example by the processes described by Naik et al. and Russo et al., supra.

Russo et al., supra., discloses 2-thioureido-1,3,4-thiadiazole, i.e. the compound of formula (III), as an antibacterial agent. No mention of antiviral activity is made.

$R^2$ in the above formula (I) includes an acyl group defined by $-C(=S)-NH-R^3$, where $R^3$ can be another acyl moiety $-COOR^4$. This definition of $R^2$ provides the N-acyl thioureas of the invention, many of which are included in a preferred method of treatment. Such thioureas have the formula (II):

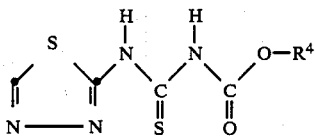

where $R^4$ has the above-defined meaning. Many of these thiadiazole thioureas are known in the art, for example as described in Japanese Pat. Nos. 71/35262, which is directed to mycocides, bacteriocides and herbicides, and 74/7218, which is directed to fungicides and bacteriocides.

In defining the foregoing compounds, $R^4$ includes "$C_1$–$C_{10}$ alkyl" and "substituted $C_1$–$C_{10}$ alkyl". These terms refer to straight and branched chain alkyl groups such as ethyl, n-hexyl, isodecyl, 6-ethylheptyl, and optionally substituted alkyls such as haloalkyl, hydroxyalkyl, phenylalkyl and the like. "Halo" includes fluoro, chloro, bromo and iodo. $R^4$ can additionally be $C_2$–$C_{10}$ alkenyl or substituted alkenyl such as allyl, 4-hexenyl, 3-chloro-5-heptenyl, 2-hydroxy-4-isoheptenyl and the like, as well as substituted phenyl such as chlorophenyl, hydroxyphenyl, methylphenyl, cyanophenyl and the like. Preferred $R^4$ groups are $C_1$–$C_6$ alkyl and $C_2$–$C_6$ alkenyl.

Most of the foregoing compounds are named herein as carbamimidothioic acid derivatives and can be prepared by reacting a 1,3,4-thiadiazol-2-ylthiourea with an alkylating agent of the formula $R^6X$ where $R^6$ is as defined above and X is a leaving group. Suitable leaving groups include Cl, Br, I, and sulfonic ester groups like tosylate and mesylate. Thus, suitable alkylating agents include, for example, an alkyl halide such as methyl bromide, or a substituted alkyl halide such as cyanomethyl bromide or 2-pyridylmethyl iodide. The reactions are typically accomplished by mixing approximately equimolar quantities of a 2-thiadiazolyl thiourea and an alkylating agent in the presence of a base such as sodium carbonate and in an unreactive organic solvent such as dimethylformamide of acetonitrile. The reaction is normally complete within about sixteen hours when carried out at about 20° C. to about 50° C. The reaction solvent can be removed by evaporation under reduced pressure if desired. The product is readily purified by routine methods, including crystallization from solvents such as ethanol, ethyl acetate, hexane; or chromatography over solid supports such as silica and the like.

A particularly preferred group of compounds provided by this invention includes 1,3,4-thiadiazol-2-cyanamide and its pharmaceutically acceptable salts. The compound can be prepared by reacting a carbamimidothioic acid ester with an oxidizing agent such as metachloroperbenzoic acid, peracetic acid, sodium peroxide, hydrogen peroxide, ozone, chlorine or the like.

1,3,4-Thiadiazole-2-cyanamide can also be prepared by reacting a protected 2-amino-thiadiazole derivative, namely 4-imino-3-phenylmethyl-1,3,4-thiadiazole with cyanogen bromide and then removing the protecting group at the 3-position by debenzylation with a Lewis acid, e.g. aluminum chloride. The debenzylation is carried out in an organic solvent such as methylene chloride, toluene or benzene. Preferably at least 2 equivalents of Lewis acid are used, and more preferably 4 to 8 equivalents are used. The temperature is not critical. The debenzylation can be carried out, for example, at from 0° C. to 90° C. Room temperature is preferred.

The cyanamide is also produced when a carbamimidiothioic acid ester is reacted with ammonia, as illustrated in Example 8.

The cyanamide readily forms pharmaceutically acceptable salts by reaction with organic and inorganic bases such as sodium acetate, calcium carbonate, sodium hydroxide and the like.

The compounds of this invention can exist in several tautomeric forms, all of which are included within the scope of the invention. For example, a preferred compound, 1,3,4-thiadiazol-2-cyanamide, can exist as follows:

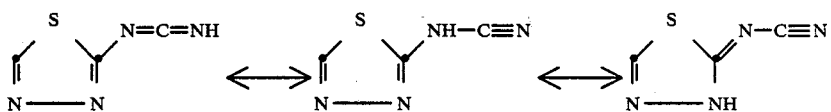

Another example of tautomeric forms of an invention compound is represented by the following formulas:

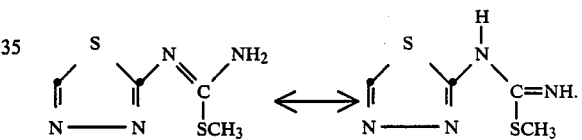

All possible tautomeric forms of the invention compounds are embraced herein.

The following detailed examples illustrate the synthesis of thiadiazoles to be employed in the antiviral method of this invention.

PREPARATION 1

[(1,3,4-Thiadiazol-2-ylamino)thioxomethyl]carbamic acid, ethyl ester

To a stirred solution of 19.2 g (190 mM) of 2-amino-1,3,4-thiadiazole in 200 ml of acetonitrile were added in one portion 25 g (190 mM) of ethoxycarbonyl isothiocyanate. The reaction mixture was stirred at 24° C. for sixteen hours. The precipitate was collected by filtration, washed three times with ethyl acetate and dried to provide 35 g (80% yield) of [(1,3,4-thiadiazol-2-ylamino)thioxomethyl]carbamic acid, ethyl ester.

Analysis calc. for $C_6H_8N_4O_2S_2$:
Theory: C, 31.02; H, 3.47; N, 24.12.
Found: C, 31.32; H, 3.27; N, 24.40.

PREPARATION 2

1,3,4-Thiadiazol-2-ylthiourea

A solution of 10 g of [(1,3,4-thiadiazol-2-ylamino)thioxomethyl]carbamic acid, ethyl ester (from Preparation 1) in 150 ml of 1N sodium hydroxide was heated at reflux for ninety minutes. The solution was cooled and concentrated by evaporation under reduced pressure.

The precipitated solid was collected by filtration and dissolved in 20 ml of water. The aqueous solution was acidified by addition of 200 ml of 1N hydrochloric acid. The product was collected by filtration and recrystallized from N,N-dimethylformamide to give 5 g of 1,3,4-thiadiazol-2-ylthiourea. m.p. 253° C. p Analysis calc. for $C_3H_4N_4S_2$:

Theory: C, 22.49; H, 2.52; N, 34.97; S, 40.02.
Found: C, 22.73; H, 2.33; N, 34.74; S, 40.26.

EXAMPLE 1

$N^1$-1,3,4-thiadiazol-2-ylcarbamimidothioic acid, methyl ester

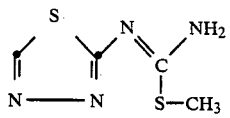

A mixture of 4.8 g of 1,3,4-thiadiazol-2-ylthiourea (from Preparation 2) in 45 ml of 1N sodium hydroxide, 15 ml of ethanol and 4 ml of methyl iodide was heated at 40° C. for ten minutes. The mixture was acidified by adding 50 ml of 1N hydrochloric acid. The reaction mixture was concentrated by evaporation under reduced pressure. The precipitated solid was collected by filtration and dried to give 3.02 g of $N^1$-1,3,4-thiadiazol-2-ylcarbamimidothioic acid, methyl ester. m.p. 116°-117° C.

Analysis calc. for $C_4H_6N_4S_3$:
Theory: C, 27.57; H, 3.47; N, 32.15; S, 36.80.
Found: C, 27.78; H, 3.55; N, 31.92; S, 36.54.

$^1$Hnmr (300 MHz) ($D_6DMSO/Me_4Si$) ∂ 2.42 (s, 3H, S—$CH_3$), 8.90 (broad s, 2H, $NH_2$) 9.08 (s, 1H, ring H) FD mass spec., parent ion 174.

EXAMPLE 2

$N^1$-1,3,4-thiadiazol-2-ylcarbamimidothioic acid, ethyl ester

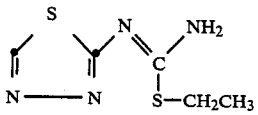

A solution of 3.2 g (20 mM) of 1,3,4-thiadiazol-2-ylthiourea in 100 ml of N,N-dimethylformamide containing 1.6 ml (20 mM) of ethyl iodide and 2.12 g (20 mM) of sodium carbonate was stirred at 24° C. for twentyfour hours. The reaction mixture was filtered and the filtrate was concentrated to an oil by evaporation of solvents under reduced pressure. The oil was chromatographed over a Waters prep. 500 column, eluting with 75% ethyl acetate/hexane (v/v). The appropriate fractions were collected, concentrated to dryness to leave a solid which upon crystallization from diethyl ether and hexane was identified as 2.08 g of $N^1$-1,3,4-thiadiazol-2-ylcarbamimidothioic acid, ethyl ester.

Analysis calc. for $C_5H_8N_4S_2$:
Theory: C, 31.90; H, 4.28; N, 29.76; S, 34.06.
Found: C, 32.18; H, 4.18; N, 29.59; S, 34.08.

$^1$Hnmr (300 MHz) ($D_6DMSO/Me_4Si$) ∂ 1.06 (t, 3H, $CH_3$), 3.02 (q, 2H, $CH_2$), 8.88 (broad s, 2H, $NH_2$), 9.08 (s, 1H, ring H).

ir (KBr) $cm^{-1}$: 3259.9, 3089.2, 1624.2, 1510.4, 1416.8, 1377.3, 1347.4, 1247.1, 1209.5, 718.5.

FD mass spec.: 188.

EXAMPLES 3-5

The following thiadiazolylcarbamimidothioic acid esters were prepared by reacting 1,3,4-thiadiazol-2-ylthiourea with an alkyl halide according to the procedures of Examples 1 and 2.

$N^1$-1,3,4-thiadiazol-2-ylcarbamimidothioic acid, n-butyl ester; yield 1.68 g; mp 40° C.

$^1$Hnmr (300 MHz) ($D_6DMSO/Me_4Si$) ∂ 0.90 (t, 3H, $CH_3$), 1.38 (sextet, 2H, —$CH_2$—), 1.60 (pentet, 2H, —$CH_2$—), 3.04 (triplet, 2H, —$CH_2$), 8.90 (broad s, 2H, $NH_2$), 9.09 (s, 1H, ring H).

FD mass spec. 216.

$N^1$-1,3,4-thiadiazol-2-ylcarbamimidothioic acid, 2-pyridinylmethyl ester, hydrochloride; yield 3.72 g.

$^1$Hnmr (300 MHz) ($D_6DMSO/Me_4Si$) ∂ 4.64 (s, 2H, $CH_2$), 7.82 (t, 1H, pyridine H), 7.98 (d, 1H, pyridine H), 8.40 (t, H, pyridine H), 8.79 (d, 1H, pyridine H), 9.11 (s, 1H, ring H).

FD mass spec. 251.

$N^1$-1,3,4-thiadiazol-2-ylcarbamimidothioic acid, cyanomethyl ester; yield 1.04 g.

$^1$Hnmr (300 MHz) ($D_6DMSO/e_4Si$) ∂ 4.14 (s, 2H, $CH_2$), 9.09 (broad s, 2H, $NH_2$), 9.15 (s, 1H, ring H).

FD mass spec. 199.

PREPARATION 3

[(1,3,4-Thiadiazol-2-ylamino)thioxomethyl]carbamic acid, phenyl ester

A solution of 3.8 g (50 mM) of ammonium thiocyanate in 100 ml of acetonitrile containing 7.8 g (50 mM) of phenyl chloroformate was stirred at 24° C. for one hour. The reaction mixture was filtered into a suspension of 6.88 g (50 mM) of 2-amino-1,3,4-thiadiazole hydrochloride in 75 ml of acetonitrile and 25 ml of propylene oxide. The reaction mixture was stirred for two hours at 24° C. and then filtered to provide a solid precipitate identified as 6.42 g of [(1,3,4-thiadiazol-2-ylamino)thioxomethyl carbamic acid, phenyl ester.

FD mass spec. 280.

PREPARATION 4-6

By following the general procedure of Preparation 3, the following products were made. [(1,3,4-Thiadiazol-2-ylamino)thioxomethyl]carbamic acid, n-hexyl ester Analysis calc. for $C_{10}H_{16}N_4O_2S_2$:
Theory: C, 41.65; H, 5.59; N, 19.43; S, 22.24.
Found: C, 41.64; H, 5.31; N, 19.28; S, 22.46.

[(1,3,4-thiadiazol-2-ylamino)thioxomethyl]carbamic acid, methyl ester

FD mass spec. 218

[(1,3,4-thiadiazol-2-ylamino)thioxomethyl]carbamic acid, vinyl ester

FD mass spec. 230.

PREPARATION 7

[(Methylthio)(1,3,4-thiadiazol-2-ylamino)methyl]carbamic acid, ethyl ester

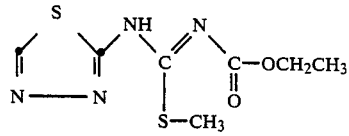

A mixture of 6.96 g (30 mM) of [(1,3,4-thiadiazol-2-ylamino)thioxomethyl]carbamic acid, ethyl ester (prepared as described in Preparation 1) in 45 ml of 1N sodium hydroxide containing 9.0 g (4 ml) of methyl iodide and 15 ml of methanol was heated at 40° C. for ten minutes. The reaction mixture was cooled to 5' C. and filtered. The filter cake was washed with water and air dried to provide 4.72 g of [(methylthio)(1,3,4-thiadiazol-2-ylamino)methyl]carbamic acid, ethyl ester.

Analysis calc. for $C_7H_{10}N_4O_2S_2$:
Theory: C, 34.13; H, 4.09; N, 22.75; S, 26.04.
Found: C, 34.41; H, 3.84; N, 22.91; S, 25.94.

PREPARATION 8

[(Ethylthio)(1,3,4-thiadiazol-2-ylamino methyl]carbamic acid, ethyl ester

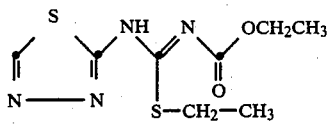

[(1,3,4-Thiadiazol-2-ylamino)thioxomethyl]-carbamic acid, ethyl ester (6.96 g) was reacted with 4 ml of ethyl iodide according to the procedure of Prepartion 7 to give 1.83 g of [(ethylthio) (1,3,4-thiadiazol-2-ylamino)-methyl]carbamic acid, ethyl ester.

FD mass spec. 260.

EXAMPLE 6

1,3,4-Thiadiazole-2-cyanamide

A solution of 3.48 g (20 mM) of $N^1$-1,3,4-thiadiazol-2-ylcarbamimidothioic acid, methyl ester (prepared as described in Example 1) in 200 ml of dichloromethane containing 4 g (20 mM equivalents based on 85% purity) of meta-chloroperbenzoic acid was stirred at 24° C. for two hours. The mixture was filtered and the precipitate was then stirred with 40 ml of water for two hours. The solid was collected by filtration and dried to give 1.7 g of 1,3,4-thiadiazole-2-cyanamide.

FD mass spec.: 126
Analysis Calc. for $C_3H_2N_4S$:
Theory: C, 28.57; H, 1.60; N, 44.42; S, 25.42.
Found: C, 28.95; H, 1.80; N, 43.60; S, 24.87.

EXAMPLE 7

1,3,4-Thiadiazole-2-cyanamide Sodium salt

To a solution of 1.38 g of 1,3,4-thiadiazole-2-cyanamide in 10.5 ml of 1N sodium hydroxide were added 100 ml of ethanol. The mixture was filtered and the solvent was removed from the filtrate to provide an oil. The oil was crystallized from 20 ml of methanol and 100 ml of isopropyl alcohol by slowly removing the methanol by evaporation under reduced pressure to produce 980 mg of the sodium salt of 1,3,4-thiadiazole-2-cyanamide.

$^1$Hnmr (300 MHz) ($D_6$DMSO/Me$_4$Si) ∂ 8.68 (s, 1H, ring H).
FD mass spec.: 126.
Analysis calc. for $C_3HN_4SNa$:
Theory: C, 24.33; H, 0.68; N, 37.83; S, 21.65.
Found: C, 24.59; H, 0.87; N, 38.06; S, 21.90.

EXAMPLE 8

1,3,4-Thiadiazole-2-guanidine

A mixture of 5.0 g of N'-1,3,4-thiadiazol-2-ylcarbamidothioic acid, methyl ester (from Example 1) in 50 ml of ammonia and 100 ml of ethanol was heated in a bomb at 140° C. for 14 hours. TLC on silica gel plates (66% CHCl$_3$, 26% MeOH, 8% HOAc) showed 2 new spots, one of which ran identically with 1,3,4-thiadiazole-2-cyanamide (Example 6). Solvent was removed by evaporation and the crude material was stirred with 200 ml of 1N HCl and filtered to remove the insoluble cyanamide. The HCl solution was evaporated to dryness and the residue purified by reverse phase HPLC, eluting with 90% MeOH/H$_2$O to give 1.5 g of 1,3,4-thiadiazole-2-guanidine.

$^1$Hnmr (300 MHz) ($D_6$DMSO/Me$_4$Si) ∂ 8.37 (broad s, 4H, NH$_2$), 9.27 (s, 1H, ring H).
FD mass spec.: 144.

EXAMPLE 9

1,3,4-Thiadiazole-2-cyanamide

A. Benzylation of 2-amino-1,3,4-thiadiazole

A mixture of 101 g of 2-amino-1,3,4-thiadiazole, 650 ml of n-propanol, and 140 ml of benzyl bromide was heated in a 2 L flask. When the temperature of the reaction mixture reached 88° C., all of the 2-amino-1,3,4-thiadiazole was in solution. At 98° C. the solution began refluxing and the flask was removed from the heating mantel and placed in a water bath to control the refluxing. A 250 ml additional portion of n-propanol was added to maintain fluidity of the mixture, and the mixture was stirred for 2 hours, heating when necessary to maintain a temperature of 86° C. The mixture was then cooled to 30° C. The product, 4-imino-3-(phenylmethyl)-1,3,4-thiadiazole hydrobromide was collected, rinsed with n-propanol, and air dried. Yield 190 g (70%), m.p. 200°–202° C.

B. Reaction with cyanogen bromide

To a stirred mixture of 146 g of 4-imino-3-phenyl-methyl-1,3,4-thiadiazole hydrobromide, 1 L of water, and 1 L of ethyl acetate, 44 ml of a 50% by weight solution of sodium hydroxide in water was added to dissolve the thiadiazole starting material. The aqueous layer was then separated and discarded. To the remaining ethyl acetate solution, 800 ml of water containing 84 g of sodium bicarbonate was added. To this solution, a solution of 56.3 g of cyanogen bromide in 150 ml of ethyl acetate was added dropwise over 25 minutes. The mixture was stirred a further 30 minutes. Then, the aqueous layer was separated and discarded. The remaining ethyl acetate solution was washed with 200 ml of water. A saturated salt solution was added to speed separation of the layers, and the aqueous layer was then separated and discarded. The ethyl acetate solution was concentrated down to one third of its original volume, and then 100 ml of toluene was added. This mixture was concentrated down to about one third its original volume, and another 100 ml of toluene was added. This concentration procedure was repeated several times, producing the desired (3-phenylmethyl-1,3,4-thiadiazole-2(3H)-ylidene) cyanamide as a precipitate, which was isolated by filtration, washed with toluene and dried. Yield 57.7 g (50.6%).

C. Debenzylation

Six equivalents (7.4 g) of finely ground aluminum chloride was added to a mixture of 2.0 g of (3-phenylmethyl-1,3,4-thiadiazole-2(3H)-ylidene) cyanamide in 50 ml of methylene chloride. The mixture was stirred for 2 hours, and 50 ml of THF was added. The mixture was then poured into 50 ml of cold water, stirred for ten minutes, and filtered to remove insolubles. Then about 5 g of sodium chloride was added to the mixture to aid separation of the layers and the THF layer was separated. An additional 2 g of salt was added to the aqueous layer, and two extractions with 25 ml portions of THF were carried out. The THF layers were combined, dried with magnesium sulfate, and concentrated to a solid. A 25 ml portion of methylene chloride was added to the solid, then the solid was collected and dried, providing 0.91 g of 1,3,4-thiadiazole-2-cyanamide (yield 78%), which was shown to be 96.7% pure by HPLC (m.p. 155d).

The thiadiazoles defined above have demonstrated antiviral activity in standard tests and thus can be employed to treat or prevent diseases commonly caused by a wide range of viruses. While the thiadiazoles have not demonstrated activity against all viruses at the levels tested. The compounds nevertheless possess a wide spectrum of antiviral utility. Typical viruses against which the thiadiazoles have shown in vitro and/or in vivo activity include those of the orthomyxovirus family, such as the various strains of influenza and the like; the paramyxovirus family, such as the various strains of parainfluenza, measles, Respiratory Syncytial Virus (RSV), Canine Distemper Virus (CDV) and the like; the poxvirus family, such as Vaccinia and the like; the herpes virus family, such as Herpes Simplex I (HSV I) and Herpes Simplex Virus II (HSV II) and the like; as well as viruses such as Semliki Forest and Enteric Cytopathogenic Human Orphan type 25 (ECHO 25).

It is interesting to note, that among the members of the picornavirus family the thiadiazoles have shown activity against ECHO 25, but have failed to demonstrate antiviral activity against certain other members of that family, such as the rhinoviruses and the polioviruses. In addition, preliminary testing of at least one thiadiazole of the invention (the compound of Example 7) has failed to demonstrate conclusive activity against retroviruses such as HIV and Friend Leukemia. The thiadiazoles have shown mixed in vitro activity against Vesicular Stomatitus Virus since the compound of Preparation 2 displays in vitro activity while, so far, the compound of Example 7 does not. However, the thiadiazoles have shown excellent in vivo and/or in vitro activity against all strains of influenza tested.

A preferred group of viruses against which the thiadiazoles have shown activity are the various strains of influenza viruses, as well as other viruses such as parainfluenza, measles, RSV, CDV, Semliki Forest, Vaccinia, HSV I, HSV II and ECHO 25.

A most preferred group of viruses against which the thiadiazoles have shown activity are the various strains of influenza, HSV I, HSV II and parainfluenza, as well as other viruses such as ECHO 25, RSV, measles, Semliki Forest and Vaccinia.

The most preferred antiviral method of the present invention employs an antiviral amount of a thiadiazole as defined above against the various strains of influenza virus. In particular, the thiadiazoles of the present invention have shown good in vitro and/or in vivo activity against influenza viruses such as A1-Ann Arbor, A1-FM, A-NWS, A-GY, A-Brazil, A-X-15, A-Texas, B-Taiwan and B-Massachusetts. A preferred group of influenza viruses against which the thiadiazoles have shown activity are A1-Ann Arbor, A-NWS, A2-Hong Kong, B-Great Lakes, B-Taiwan, B-Maryland, B-Hong Kong, B-Singapore, A-Brazil, A-Texas, and A-Fukushima.

The thiadiazole antiviral agents contemplated by this invention have exhibited their antiviral activity both in vitro and/or in vivo. Sometimes, as is often the case when testing compounds for in vivo antiviral activity, the experimental results may vary due to differences in the types of test animals employed, differences in the methods of administration and dosage rate, as well as problems associated with the handling of viruses in general. Such variation is expected and does not detract from the conclusion that the thiadiazole antiviral agents of the invention possess in vivo antiviral activity. Their in vivo activity against influenza A1-Ann Arbor strain is particularly well-documented.

In an in vivo test series, groups of eighteen CD-1 mice were challenged with a predetermined dose of influenza A1-Ann Arbor strain. A predetermined dose of the thiadiazole was also administered, and one group that was given vehicle alone served as a control.

The test continued for 10 days. The number of animals dying in each group on each day was recorded. The animals living at the end of 10 days were considered survivors. The "survival index" method was then used to analyze the data. This analysis is carried out as follows.

From the data for the control group, a survival index value ($SI_{DayX}$) is assigned to each day (X), starting with the day on which a death first occurs in the control group (typically on Day X=4), and continuing through day 10. The survival index value for the day on which a death first occurs is defined to be zero. The values for the remaining days through day 10 are calculated using the formula $$SI_{Day\ X} = (X - 1)\left[\frac{\text{Number of Control Animals Dying on Day } (X - 1)}{\text{Total Number of Control Animals}}\right] + SI_{Day\ X-1}$$

For example, if the first day on which a control animal dies is day 4, and 4 of 18 control animals die on day 4, then $SI_{Day\ 4}$=Zero, and $$SI_{Day\ 5} = (5-1)\ 4/18 + 0 = 16/18 = 0.88$$

A survival index value for survivors, "S.I. survivors" is also calculated from data for the control animals, using the formula $$SI_{survivors} = 10\left[\frac{\text{Number of Control Animals Dying on Day 10}}{\text{Total Number of Control Animals}}\right] + SI_{Day\ 10}$$

The resulting set of calculated index values is then used to assign average survival values both to the control group and to each group of tested animals using the following procedure. The average survival value for the control group, "$SI_{controls}$", is calculated by multiplying each $SI_{DayX}$ value by the number of control animals dying on the corresponding day (X), multiplying the $SI_{survivors}$ value by the number of survivors, if any, summing these products, and dividing the sum by the total number of control animals. The average survival value for a treated group, "$SI_{treated}$", is calculated by multiplying each $SI_{DayX}$ value by the number of treated animals dying on the corresponding day (X), multiplying $SI_{survivors}$ by the number of surviving treated animals, summing these products, and dividing the sum by the total number of treated animals.

Next a comparison with the control group is calculated by the following formula where P=percent of maximum.

$$P = \frac{SI\ treated - SI\ controls}{SI\ survivors - SI\ controls} \times 100$$

Using this formula, if the average survival value for the treated animals is only equal to the average survival value for the controls, then P=0%. If the average survival value for the treated animals is equal to the survival index value for survivors, then P=100%.

This percent of maximum is then allocated to a relative activity index RA as follows:

| P | | RA |
|---|---|---|
| 10% or less = 1 | | (borderline) |
| 20–40% = 2 | | (slightly active) |
| 40–60% = 3 | | (moderately active) |
| 60–80% = 4 | | (good activity) |
| 80–100% = 5 | | (very active) |

The following Table I gives RA values for representative compounds of this invention.

TABLE I

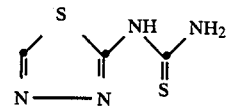

| R⁴ | RA |
|---|---|
| CH₂CH₃ | 4.5 |
| CH₃ | 5 |
| phenyl | 5 |
| n-hexyl | 5 |
| vinyl | 4 |

| R⁵ | R³ | RA |
|---|---|---|
| S—CH₂CH₃ | H | 5 |
| S—CH₃ | H | 5 |
| S—CH₃ | —C(=O)—OCH₂CH₃ | 5 |
| S—CH₂CH₃ | —C(=O)—OCH₂CH₃ | 5 |
| S—CH₂CH₂CH₂CH₃ | H | 5 |
| S—CH₂—C≡N | H | 2.5 |

TABLE I-continued

| S—CH₂—2-pyridyl | H | 2.5 |

The compounds have additionally demonstrated good in vivo activity against a wide variety of influenza strains in the mouse influenza assay. Again, due to the nature of in vivo antiviral tests the in vivo antiviral influenza activity of the compounds can vary. Therefore, Table II shows representative activity of the compound of Preparation 2 over a wide dose range when administered orally in the diet to mice infected with various influenza A and B strains. The table shows the number of animals surviving over the number of animals tested (S/N) for each test group. A typical test would run for at least ten days.

TABLE II

| | | Dose (mg/kg/day) | | | |
|---|---|---|---|---|---|
| Influenza Strain | Control | 15 | 30 | 60 | 120 |
| B-Great Lake | 3/36 | 11/18 | 16/18 | 17/18 | 18/18 |
| B-Taiwan | 1/36 | 4/18 | 15/18 | 18/18 | 18/18 |
| B-Maryland | 14/50 | — | — | 19/20 | 20/20 |
| B-Hong Kong | 4/50 | — | — | 10/20 | 16/20 |
| Al-Ann Arbor | 0/50 | — | — | 20/20 | 20/20 |
| A-Texas | 8/36 | 5/18 | 8/18 | 12/18 | 16/18 |
| A-Brazil | 10/28 | 5/15 | 5/16 | 12/18 | 14/18 |

Note:
(—) means not evaluated at that dose level in the specific test shown

Plague-reduction studies provide a quantitive evaluation of inhibitors of virus multiplication in a tissue culture cell in vitro system.

In this test, susceptible MDCK cells, were grown in 25 cm² Falcon flasks at 37° C. in Medium 199 with 5 percent inactivated fetal bovine serum (FBS), penicillin (300 units/ml) and streptomycin (300 μg/ml). When confluent monolayers were formed, growth medium was removed and 0.3 ml of an appropriate dilution of virus was added to each flask. After adsorption for one hour at room temperature, the infected cell sheet was overlaid with equal parts of 1 percent Agarose and 2 X Medium 199, 2.5 percent FBS, Penicillin, and streptomycin. Varying concentrations of tested compound were incorporated in the agar overlay. The compounds were dissolved in dimethyl sulfoxide (DMSO) at a concentration of 10,000 μg/ml and then an aliquot was diluted to the desired concentration with the agar medium mixture. Flasks were incubated until control flasks indicated optimum plaque size (2-10 mm). A solution containing 10 percent formulin and 2 percent sodium acetate was added to each flask to inactivate the virus and fix the cell sheet to the plastic surface. The plaques were counted after staining the surrounding cell areas with crystal violet. Results from duplicate flasks at each concentration were averaged and compared with control flasks. The inhibition of plaque formation by 50 percent (IC₅₀) was estimated by plotting all results from 10 to 90 percent inhibition. Results for three influenza strains are reported in Table III.

TABLE III

In Vitro Activity Against Influenza Viruses
IC₅₀ (MCG/ML)

| Compounds | A-NWS | Al-Ann Arbor | B-Great Lake |
|---|---|---|---|
| Preparation 1 | 43 | | >50 |
| Preparation 2 | 3.6 | >50 | 7.0 |
| Preparation 3 | <1.6 | | |
| Preparation 7 | 75.5 | | |
| Preparation 8 | >50 | | |
| Example 1 | 16.3* | 0.68 | 16.3 |
| Example 2 | 18.9 | | 9.5 |
| Example 3 | 21.3* | | >50 |
| Example 4 | >50 | | >50 |
| Example 6 | 0.78 | 0.85 | 2.25 |
| Example 7 | 0.58 | 0.82 | 1.00 |
| Example 8 | | 0.02 | 0.27 |

*One test indicated the in vitro activity was >50. This test result was not incorporated with the other test results when determining the numbers reported above.

As previously mentioned, in vivo antiviral test results may vary due to numerous factors. Table IV shows the variability which can occur when different test animals and modes of administration are employed. The compounds of Examples 1 and 7 were tested against several different viruses using different kinds of test animals and different modes of oral and topical administration. In Table IV below, Column 1 indicated the test compound, while Column 2 discloses the virus the compound was employed against. Columns 3 and 4 describe the test animal and the method of administration, respectively. Finally, Column 5 discloses whether or not antiviral activity was shown. In column 5, a compound was considered to show antiviral activity if, at the end of the test; the number of surviving animals which had been treated with test compound was greater than the number of surviving control animals (mouse); the animals receiving treatment with test compound showed a reduction in nasal washing virus titer relative to the control animals (hamster, african green monkey); the animals receiving treatment with test compound had fewer lesions than the control animals (guinea pig).

TABLE IV

Comparison of In Vivo Test Systems

| Compound | Virus | Test Animal | Administration | Result |
|---|---|---|---|---|
| Example 1 | RSV | hamster | drinking water | active |
| Example 7 | RSV | hamster | food | active |
| Example 1 | HSV I | mouse | drinking water | active |
| Example 7 | HSV I | mouse | drinking water | active |
| Example 1 | Parainfluenza (type 3) | african green monkey | gavage | no activity shown |
| Example 1 | HSV II | guinea pig | topical cream | no activity* shown |
| Example 7 | HSV II | guinea pig | topical cream | active |

*Result not unexpected since biologically the compound of Example 1 is converted to a salt form of the compound of Example 6 (the compound of Example 7 is the sodium salt form of the compound of Example 6) in vivo. Such a conversion probably does not occur in the topical method of administration.

For comparison purposes, Table V provides the results of an in vitro study of the activity of the compounds of Examples 1 and 7 against some of the viruses detailed in Table IV. In vitro activity against some additional viruses is also included. The in vitro study was performed using a plaque-reduction test system similar to that described previously with respect to Table III, with the major difference between the two systems being that for the plaque-reduction test system used to obtain the results reported in Table V, cell lines other than MDCK were used. The inhibition of plaque formation by 50 percent (IC₅₀) was estimated by plotting all results from 10 to 90 percent inhibition. The in vitro test results are reported in Table V.

TABLE V

In Vitro Activity Against Selected Viruses

| Virus | Cell Line | Example 1* | Example 7 |
|---|---|---|---|
| Herpes I | BSCl | 9.6 | 2.95 |
| Parainfluenza (type 3) | BSCl | 4.5 | .14 |
| Parainfluenza (type 3) | HELA | >25 | .72 |
| Herpes II | BSCl | | .19 |
| Semliki Forest | BSCl | 43.0 | <.23 |
| Vaccinia | BSCl | 15.8 | <.31 |
| Vaccinia | VERO | | .29 |

*The compound of Example 1 is converted in vivo to a salt form of the compound of Example 6 (the compound of Example 7 is the sodium salt form of the compound of Example 6).

For in vitro use, the compounds can be added to a tissue culture to suppress viral growth therein. The compounds can also be used to treat and prevent viral diseases in plants and animals.

The preferred manner of using the compounds is for in vivo use, whereby the compounds can be administered either parentally, topically, orally, or by inhalation or the intranasal route to a mammal suffering from a viral infection or susceptible thereto. For parenteral administration, as by the intraperitoneal route, the compound may be dissolved or suspended in water containing 2% of a surface active agent, particularly an emulphor (a polyhydroxylated fatty acid). Oral administration is, of course, preferred. For such use, a compound as defined herein is mixed with one or more standard pharmaceutically-acceptable extending media such as starch, sucrose, lactose, calcium carbonate, etc., and the mixture loaded into empty telescoping gelatin capsules, such that each capsule contains an amount of a compound effective to suppress the growth of influenza or other virus, either prospective or present. In other words, the compounds can be used prophylactically or as curative agents. Alternatively, the drug can be mixed with various excipients including starch, lubricating agents, wetting agents, etc., such as stearic acid, magnesium stearate and the like, and the mixture pressed into tablets, each tablet containing an amount of the drug effective to abort or cure an attack of influenza or other virus. Such tablets can be scored so as to provide half or quarter dosages where the drug is to be administered to children. The compounds can also be administered in solution or suspension.

To practice the antiviral method of this invention, all that is required is that an antiviral amount of a thiadiazole antiviral agent be added to the tissue culture to be protected, or be administered to an animal or plant suffering from or susceptible to a viral infection. The compounds will ideally be formulated with pharmaceutically acceptable diluents for convenient administration, for example orally, topically or parenterally, and can be employed for prophylatic as well as therapeutic treatment. The formulations will normally contain from about 1 to about 95 percent by weight of active thiadiazole antiviral agent.

For oral administration, the compounds will be formulated with common diluents and excipients such as sucrose, starch, microcrystalline cellulose, acacia and the like, and molded into tablets or pills or encapsulated into gelatin capsules, or formulated as solutions, elixirs, lozenges or the like. Topical formulations will include mixing the thiadiazole antiviral agent with excipients such as bees wax, lanolin, oil and the like for ready formulation as ointments, salves, creams, tinctures, lotions, patches and the like.

For severe viral infections, the antiviral thiadiazoles will be formulated for intravenous or intramuscular administration. Such formulations will contain from about 1 to about 50 percent active agent. The compounds will be dissolved in common diluents such as isotonic saline of dextrose solutions, for intravenous infusion, and can be dissolved in polyhydric aliphatic alcohols such as propylene glycol or polyethylene glycol for easy intravenous or intramuscular injection.

Pharmaceutically acceptable salts can be prepared from those compounds of the above formula sufficiently acidic or basic to react with common organic and inorganic acids and bases such as hydrochloric acid, succinic acid, sodium hydroxide, and the like. The pharmaceutically acceptable salts generally have enhanced solubility characteristics compared to the compound from which they are derived, and thus are often more amenable to formulation as liquids or emulsions.

The thiadiazole antiviral agents described above are active over a wide range of dose levels. While the particular dose to be administered will be determined by the precise viral infection to be treated or guarded against and its severity, the route of administration, and related circumstances that will be determined by attending medical practitioners, the normal dose will range from about 0.1 to about 100 mg/kg, and more typically about 0.5 to about 25 mg/kg.

In a preferred method of treatment, the thiadiazole compounds are administered to mammals susceptible to infection with influenza virus including horses, mice, pigs and humans. Among humans, the compounds are administered prophylactically particularly to the elderly, young children, nurses, doctors, and other hospital or public health personnel, for example when there is evidence of an imminent "flu" epidemic. The compounds can also be given to anyone having a known exposure to a person with "flu". It is a particular advantage of the therapeutic processes of this invention that the compounds may be administered either prophylactically or therapeutically to patients without a preliminary determination as to virus strain, since the compounds are effective against all strains.

The following Examples illustrate some typical formulations using compounds of Formula I.

EXAMPLE 10

| Preparation of Tablets | |
|---|---|
| The compound of Preparation 1 | 100 mg. |
| Lactose | 200 mg. |
| Corn Starch | 300 mg. |
| Corn Starch Paste | 50 mg. |
| Calcium Stearate | 5 mg. |
| Dicalcium Phosphate | 45 mg. |

The active ingredient, corn starch, lactose and dicalcium phosphate are uniformly blended. The corn starch paste is prepared as a 10 percent aqueous paste and is blended into the mixture to uniformity. The mixture is blended with the calcium stearate and then compressed into a tablet.

EXAMPLE 11

| Preparation for Suppositories | |
|---|---|
| The compound of Example 1 | 500 mg. |
| Theobromo oil | 1500 mg. |

The above ingredients are blended to uniformity at a temperature of about 60° C. and then cooled in a tapered mold.

EXAMPLE 12

| Preparation for oral suspension | |
|---|---|
| The compound of Example 7 | 500 mg. |
| Sorbitol solution (70% N.F.) | 40 mg. |
| Sodium benzoate | 150 mg. |
| Lactose | 10 mg. |
| Cherry flavor | 50 mg. |
| Ethanol | 100 ml. |

The above ingredients are combined such that each ml. of syrup contains 5 mg of active ingredient. Administration of about 5 to about 20 ml. of the syrup each day will protect a human subject from viral infections such as influenza.

EXAMPLE 13

| Intranasal Formulation | |
|---|---|
| | % by weight |
| The compound of Example 8 | 1.0 |
| Antarox (non-ionic polyoxyethylated fixed oil, GAF Corp.) | 38.5 |
| Ethanol | 10.0 |
| Freon 11 (trichloromonofluoromethane) | 25.0 |
| Freon 12 (dichlorodifluoromethane) | 25.0 |
| Menthol | 0.5 |

The active ingredient is added to the Antarox at about 70°-80° C. and the mixture is stirred until a solution is formed. The solution is cooled and diluted with a mixture of the menthol in the ethanol. The resulting solution is placed in a aerosol container and chilled to 0° C. The Freon propellants are added and the aerosol container is sealed with a valve.

We claim:

1. An antiviral method which comprises administering to an animal or cell culture which has a virus selected from the group consisting of the various strains of influenza, Herpes Simplex Virus I, Herpes Simplex Virus II, Parainfluenza, ECHO 25, RSV, measles, Semliki Forest, and Vaccinia, an antiviral amount of a compound of formula (I):

$$\begin{array}{c} S \quad R^1 \\ \diagup \diagdown \mid \\ \parallel \quad \parallel - N - R^2 \\ N \longrightarrow N \end{array} \quad (I)$$

wherein:
$R^1$ is hydrogen, and $R^2$ is cyano or $-C(=S)-NH-R^3$; or
$R^1$ and $R^2$ taken together are $=C(NH_2)_2$ or $=C(R^5)(NHR^{3'})$;
$R^3$ is $-COOR^4$;
$R^{3'}$ is hydrogen or $-COOR^4$;

$R^4$ is $C_1$–$C_{10}$ alkyl, optionally substituted with halo, hydroxy or phenyl, $C_2$–$C_{10}$ alkenyl, optionally substituted with halo or hydroxy, or phenyl, optionally substituted with halo, hydroxy, methyl or cyano; and $R^5$ is hydrogen or —S—$R^6$ where $R^6$ is $C_1$–$C_4$ alkyl, cyano-$C_1$–$C_4$ alkyl or pyridyl-$C_1$–$C_4$ alkyl, or a pharmaceutically acceptable salt thereof.

2. An antiviral method in accordance with claim 1 wherein an antiviral amount of a compound of the formula I is administered to an animal to be treated.

3. An antiviral method of claim 2 wherein the compound is selected from
[(1,3,4-thiadiazol-2-ylamino)thioxomethyl]carbamic acid, ethyl ester,
$N^1$-1,3,4-thiadiazol-2-ylcarbamimidothioic acid, methyl ester
$N^1$-1,3,4-thiadiazol-2-ylcarbamimidothioic acid, ethyl ester,
[(1,3,4-thiadiazol-2-ylamino)thioxomethyl]carbamic acid, phenyl ester
[(1,3,4-thiadiazol-2-ylamino)thioxomethyl]carbamic acid, n-hexyl ester,
[(methylthio)(1,3,4-thiadiazol-2-ylamino)methyl]carbamic acid, ethyl ester,
[(ethylthio)(1,3,4-thiadiazol-2-ylamino)methyl]carbamic acid, ethyl ester,
1,3,4-thiadiazole-2-cyanamide, or a pharmaceutically acceptable salt thereof.

4. An antiviral method of claim 3 employing 1,3,4-thiadiazole-2-cyanamide, or a pharmaceutically acceptable salt thereof.

5. An antiviral method of claim 4 employing 1,3,4-thiadiazole-2-cyanamide sodium salt.

6. An antiviral method of claim 2 wherein the animal to be treated has an influenza virus.

7. An antiviral method of claim 3 wherein the animal to be treated has an influenza virus.

8. An antiviral method of claim 4 wherein the animal to be treated has an influenza virus.

9. An antiviral method of claim 5 wherein the animal to be treated has an influenza virus.

10. An antiviral method of claim 6 wherein the animal to be treated has an influenza virus selected from the group consisting of A1-Ann Arbor, A-NWS, A2-Hong Kong, B-Great Lakes, B-Taiwan, B-Maryland, B-Hong Kong, B-Singapore, A-Brazil, A-Texas, and A-Fukushima.

11. An antiviral method of claim 7 wherein the animal to be treated has an influenza virus selected from the group consisting of A1-Ann Arbor, A-NWS, A2-Hong Kong, B-Breat Lakes, B-Taiwan, B-Maryland, B-Hong Kong, B-Singapore, A-Brazil, A-Texas, and A-Fukushima.

12. An antiviral method of claim 11 wherein the compound used to treat the influenza virus is 1,3,4-thiadiazole-2-cyanamide, or a pharmaceutically acceptable salt thereof.

13. An antiviral method of claim 12 wherein the compound used to treat the influenza virus is 1,3,4-thiadiazole-2-cyanamide sodium salt.

14. A compound of the formula (I)

wherein:
$R^1$ is hydrogen and $R^2$ is —CN; or
$R^1$ and $R^2$ combine to form $=C(NH_2)(SR^6)$ or $=C(NH_2)_2$, where $R^6$ is $C_1$–$C_6$ alkyl, cyano-$C_1$–$C_4$ alkyl or pyridyl-$C_1$–$C_4$ alkyl; or
a pharmaceutically acceptable salt thereof.

15. A compound of claim 14 wherein $R^1$ is hydrogen and $R^2$ is —CN, or a pharmaceutically acceptable salt thereof.

16. A compound of claim 15 which is 1,3,4-thiadiazole-2-cyanamide sodium salt.

17. A compound of claim 14 wherein $R^1$ and $R^2$ combine to form $=C(NH_2)_2$.

18. A compound of claim 14 wherein $R^1$ and $R^2$ combine to form $=C(NH_2)(SR^6)$.

19. A compound of claim 18 wherein $R^6$ is $C_1$–$C_4$ alkyl.

20. A compound of claim 18 wherein $R^6$ is methyl.

21. A pharmaceutical formulation comprising as active ingredient a compound of claim 14 wherein $R^1$ is hydrogen and $R^2$ is —CN, or $R^1$ and $R^2$ combine to form $=C(NH_2)(SR^6)$, or a pharmaceutically acceptable salt thereof.

* * * * *

UNITED STATES PATENT AND TRADEMARK OFFICE
CERTIFICATE OF CORRECTION

PATENT NO. : 4,835,168
DATED : May 30, 1989
INVENTOR(S) : Charles J. Paget, Jr. et al.

It is certified that error appears in the above-identified patent and that said Letters Patent is hereby corrected as shown below:

Column 5, line 31, "$C_4H_6N_4S_3$" should read --$C_4H_6N_4S_2$--.

Column 12, line 58, "formulin" should read -- formalin --.

Column 13, Line 25, "indicated" should read -- indicates --.

Column 14, line 25, "parentally" should read -- parenterally --.

Column 14, line 26, "froma" should read -- from a --.

Signed and Sealed this

Seventh Day of May, 1991

Attest:

HARRY F. MANBECK, JR.

Attesting Officer

Commissioner of Patents and Trademarks